United States Patent [19]

Schuster

[11] 4,164,212
[45] Aug. 14, 1979

[54] DEVICES FOR MENSTRUAL CYCLE PHASE DETERMINATION

[75] Inventor: Samuel R. Schuster, Wellesley, Mass.

[73] Assignee: Ovutime, Inc., Brookline, Mass.

[21] Appl. No.: 779,150

[22] Filed: Mar. 18, 1977

Related U.S. Application Data

[60] Division of Ser. No. 629,700, Nov. 7, 1975, Pat. No. 4,013,066, which is a continuation-in-part of Ser. No. 472,611, May 23, 1974, abandoned, which is a continuation-in-part of Ser. No. 300,187, Oct. 24, 1972, abandoned.

[51] Int. Cl.² .................... A61B 10/00; G01N 33/16
[52] U.S. Cl. .................................... 128/759; 73/54
[58] Field of Search ............ 128/2 W, 2 B, 2 G, 2 R, 128/361, 3, 4, 5; 73/9, 10, 55, 60, 64, 53, 54, 59

[56] References Cited

U.S. PATENT DOCUMENTS

| | | | |
|---|---|---|---|
| 1,120,624 | 12/1914 | Osborne | 73/64 |
| 1,184,880 | 5/1916 | Schleher, Jr. | 73/10 |
| 2,427,289 | 9/1947 | Lancaster | 73/9 |
| 2,623,521 | 12/1952 | Shaw | 128/2 B |
| 2,796,758 | 6/1957 | Myers et al. | 73/60 |
| 2,887,875 | 5/1959 | Curriston | 73/9 |
| 3,017,879 | 1/1962 | Sapit et al. | 128/2 W |
| 3,037,496 | 6/1962 | Melges | 128/2 W |
| 3,117,569 | 1/1964 | Wegner | 128/2 W |
| 3,132,645 | 5/1964 | Gasper | 128/3 |
| 3,438,366 | 4/1969 | Kariher et al. | 128/2 B |

OTHER PUBLICATIONS

Benis, A. M. et al., *Rheology of Biological Systems*, Charles C. Thomas, publisher, Springfield, Ill., 1973, ch. 9, pp. 218–259.

*Primary Examiner*—Kyle L. Howell
*Attorney, Agent, or Firm*—Morse, Altman, Oates & Bello

[57] ABSTRACT

An instrument for obtaining and testing a bodily mucus for determining the rheological properties of the bodily mucus in order to ascertain menstrual cycle phase comprises a sample collecting probe and a bearing member. A mucus sample from a bodily cavity is obtained by inserting the sample collecting probe into the cavity. The working end of the probe on which the mucus sample is collected defines an inner bearing element having an outer bearing surface of predetermined grit, the mucus sample being carried on the outer bearing surface. The bearing member is provided with an outer bearing element having an inner bearing surface of predetermined grit. The inner bearing element is received within the outer bearing element in such a manner that the mucus sample introduced between the outer bearing surface and the inner bearing surface is extruded therebetween. One bearing element is biased and the other bearing element is fixed. Mechanical movement or the absence of such movement of the biased bearing element relative to the fixed bearing element is indicative of the menstrual cycle phase.

1 Claim, 10 Drawing Figures

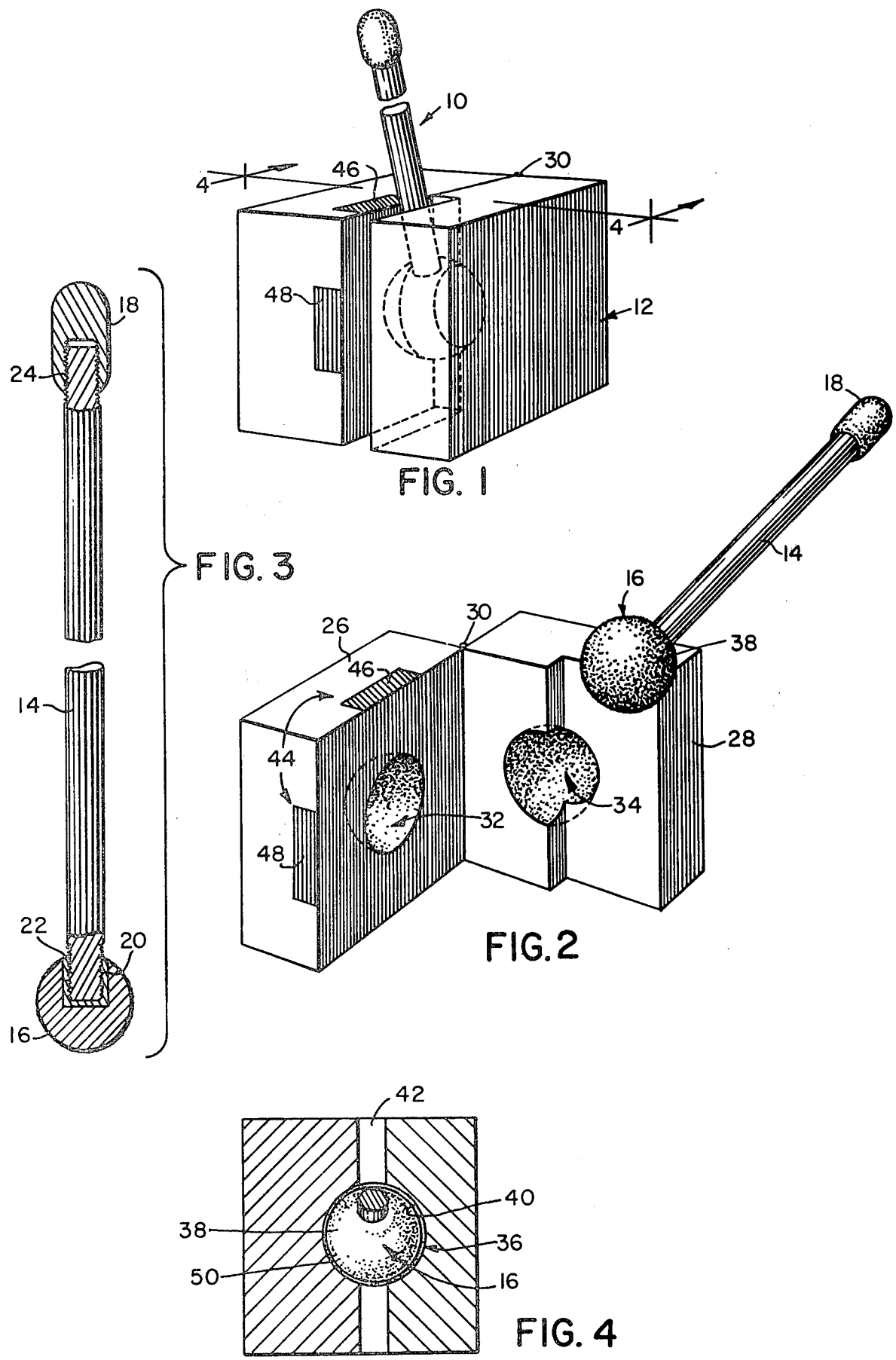

DEVICES FOR MENSTRUAL CYCLE PHASE DETERMINATION

CROSS-REFERENCE TO RELATED APPLICATIONS

This is a division of application Ser. No. 629,700, filed Nov. 7, 1975, now U.S. Pat. No. 4,013,066, issued Mar. 22, 1977, which was a continuation-in-part of Ser. No. 472,611, filed May 23, 1974, now abandoned, which was in turn a continuation-in-part of Ser. No. 300,187, filed Oct. 24, 1972, now abandoned.

BACKGROUND OF THE INVENTION

1. Field of Invention

The present invention relates to processes and devices for menstrual cycle phase determination and, more particularly, is directed towards processes and devices for obtaining bodily mucus, chiefly cervical mucus and/or oral mucus, and for determining the rheological properties of the bodily mucus in order to predict and indicate the inception and the presence of ovulation for conception control.

2. Description of the Prior Art

It has been found that mucus samples from the vaginal and oral cavities undergo distinct in-phase rheological changes during the menstrual cycle. Although the changes in the cervical mucus are much more noticeable than the changes in the oral mucus, both changes are readily determinable. During the immediate preovulatory phase, for a period of one to three days under estrogen domination, the mucus is profuse and watery. During the postovulatory phase, under progestation, the mucus becomes less abundant and highly viscous. In healthy women with normal menstrual cycles, as is well documented in the medical literature, ovulation usually occurs between the 12th and 14th day prior to the next menstrual period. Specifically, cervical mucus is most hydrated (97 to 98% water) at the time of ovulation and is relatively dehydrated (80 to 90% water) at other times. The solid residue present after desiccation may range from 2% during ovulation to 20% at other times, a ten fold increase. Determining ovulation on the basis of the preceeding menstrual period, such as in the rythm method of counting the days ellapsed between the termination of the menstrual period phase and the presumed midcycle ovulatory phase, is prone to errors because of the great variability of this determination. Although it is possible to preduct ovulation on the basis of hormonal changes in the blood or chemical changes in the mucus, present procedures for such analyses have had limited use. Since present procedures are lengthly and costly, they are utilized only in special cases. At present, there are no known reliable on-the-spot techniques that are capable of providing the information necessary for prediction or confirmation of ovulation during or immediately following examination of a patient.

SUMMARY OF THE INVENTION

The primary object of the present invention is to provide processes and devices for obtaining and testing a bodily mucus sample in order to determine menstrual cycle phase by introducing the mucus sample between inner and outer bearing elements, one of which is fixed and the other which is biased, both bearing elements having bearing surfaces of predetermined grit. Relative mechanical movement or the absence of such movement of the biased bearing element relative to the fixed bearing member denotes the menstrual cycle phase and provides indicia of ovulation. The device comprises a sample collecting probe having an inner bearing element at a working end and a bearing member having a pair of relatively movable sections formed with an inner cavity defining an outer bearing element. The mucus sample is obtained by inserting the sample collecting probe into a bodily cavity and collecting the mucus sample on the inner bearing element, the mucus sample carried on the outer bearing surface thereof. The inner bearing element is received within the outer bearing element. The mucus sample is supplied to the bearing surface of the outer bearing element while the sections are separated and the mucus sample is extruded between the bearing surfaces when the sections assembled. One of the bearing elements is held in a fixed position and the other bearing element is biased by means of a biasing element which exerts sufficient force to cause relative movement between the bearing members when the viscosity of the mucus sample is low and of insufficient force to cause such relative movement when the viscosity of the mucus sample is high. The mucus sample is characterized by low viscosity during the ovulation phase of the menstrual cycle and is characterized by high viscosity at other times during the menstrual cycle. In accordance with the teachings of the present invention, it has been discovered that the foregoing operation requires that each of the inner and outer bearing surfaces are characterized by a grit size of 200 to 800 grains per square inch. Although the scientific basis for the foregoing requirement is not understood with certainty, it is believed that this specific surface roughness controls slippage of the mucus with respect to the bearing surfaces and ensures the occurrence of predetermined shear within the mucus interior.

Other and further objects of the present invention will in part be obvious and will in part appear hereinafter.

The invention accordingly comprises the processes and devices, together with their steps, parts and interrelationships that are exemplified in the following detailed disclosure, the scope of which will be indicated in the appended claims.

BRIEF DESCRIPTION OF THE DRAWINGS

For a fuller understanding of the nature and objects of the present invention, reference should be had to the following detailed description, taken in connection with the drawings, wherein:

FIG. 1 is a perspective view of a device made in accordance with the teachings of present invention with parts in an operative relationship for the performance of certain steps of a process of the present invention;

FIG. 2 is a perspective view of the device of FIG. 1 with the parts in an inoperative position;

FIG. 3 is a sectional view of the probe of FIG. 1;

FIG. 4 is a sectional view taken along the lines 4—4 of FIG. 1;

DESCRIPTION OF THE PREFERRED EMBODIMENT

Figure 5:
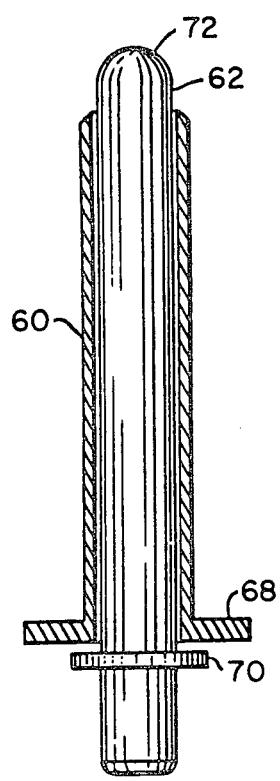
FIG. 5 is a sectional view in side elevation of an alternate embodiment of the invention showing an instrument having a core in position.
Figure 6:
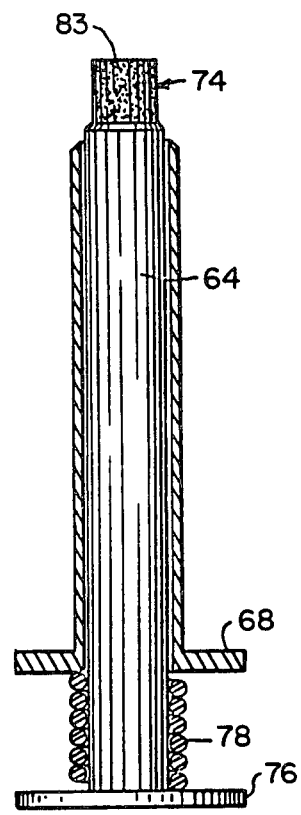
FIG. 6 is a view similar to FIG. 5, but showing the core replaced by a plunger which is in an extended position.
Figure 7:
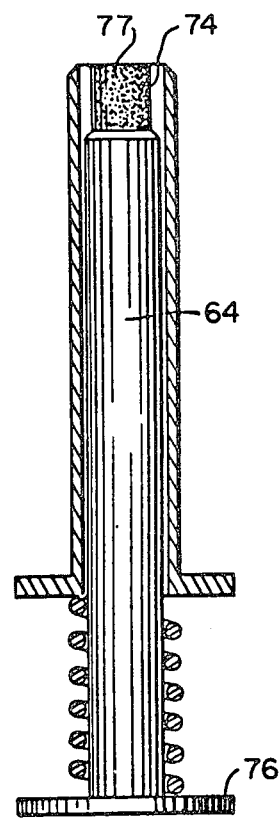
FIG. 7 is a view similar to FIG. 6, but showing the plunger in a retracted position.
Figure 8:
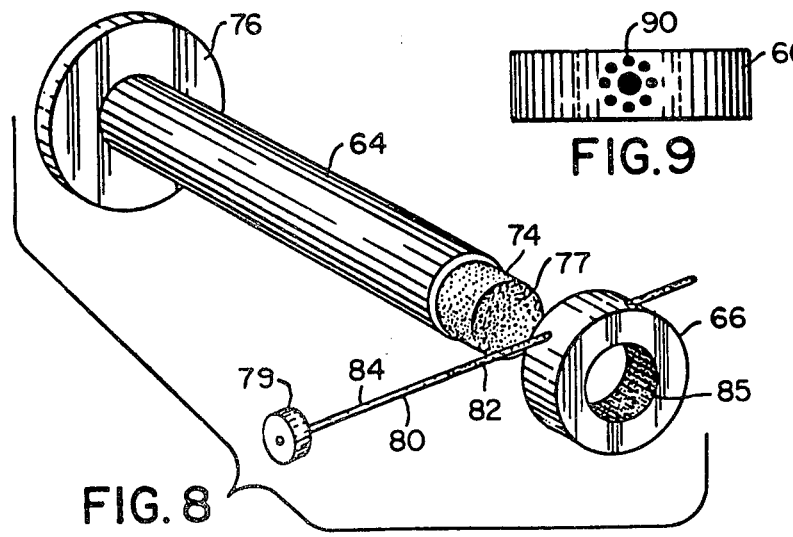
FIG. 8 is an exploded view in perspective showing the plunger and a viscometer ring.

In the drawings, FIGS. 1-4 show a device for obtaining and testing a bodily mucus, such as cervical mucus or oral mucus, to provide an indication of menstrual cycle phase, and FIGS. 5-10 show alternate embodiments of the invention for obtaining and testing cervical mucus for menstrual cycle phase determination.

Generally, the device of FIGS. 1-4 comprises a probe 10 and a bearing member 12. Probe 10 includes a medial shank portion 14 having a bearing element 16 at a working end thereof and a bias element 18 at the other end. In the illustrated embodiment, by way of example, shank 14, which is composed of a dimensionally stable, sterilizable material, for example, a plastic material such as methyl methacrylate or polycarbonate or a metallic material such as stainless steel, is externally threaded at its ends. Bearing element 16 is provided with a socket 20 within which an internally threaded sleeve 22 composed of a plastic or a metal, for example, is frictionally secured. The threaded working end of shank 14 is turned into sleeve 22. Bias element 18, composed of a metal or a plastic, for example, is provided with an internally threaded socket 24 within which the threaded free end of shank 14 is turned a specified amount so as to precisely adjust the position of bias element 18 relative to bearing element 16.

Bearing member 12 includes a pair of relatively movable sections 26, 28. In the illustrated embodiments, sections 26, 28 have substantially rectangular profiles and are interconnected by means of a fastener 30, for example a hinge. Sections 26, and 28 are provided with internal cavities 32 and 34, respectively, which are in juxtapositional registration when the sections are in the closed or operative position shown in FIGS. 1 and 4. Registered cavities 32 and 34 define a bearing element 36 which is adapted to receive bearing element 16. An outer bearing surface 38 of bearing element 16 and an inner bearing surface 40 of bearing element 36 snugly and rotatably fit each other when sections 26 and 28 are in the operative position. Section 26 is cut-away to form a guide channel 42 for shank 14.

In accordance with the present invention, each of bearing surfaces 38, 40 require a grit size ranging from 200 to 800 grains per square inch and preferably from 400 to 600 grains per square inch. Also the spacing or tolerance between the bearing surfaces 38,40 ranges from 0.01 to 10.0 mils and preferably from 1 to 5 mils. Preferably the diameter of bearing element 16 ranges from 0.25 to 2.0 inches. Preferably, each of bearing elements 16 and 36 is composed of a dimensionally stable, sterilizable material, for example, a vitreous material such as glass, a metallic material for example, a vitreous material such as glass, a metallic material such as stainless steel, or a plastic material such as methyl methacrylate.

Section 28 is provided with indicia 44 on its periphery adjacent guide channel 42. As viewed in FIGS. 1 and 2, by way of example, indicia 44 include a green segment 46 and a red segment 48 at the upper and side faces, respectively, of section 26. As hereinafter described, when probe 10 and bearing member 12 are constrained for relative movement in the operative position and a mucus sample 50 is introduced between inner bearing surface 40 and outer bearing surface 38, bias element 18 is in position to cause rotary motion of probe 10 with respect to bearing member 12. Bias element 18 is capable of exerting sufficient force to cause relative movement between probe 10 and bearing member 12 when the viscosity of mucus sample 50 is low, but is incapable of exerting sufficient force to cause relative movement between probe 10 and bearing member 12 when the viscosity of mucus sample 50 is high. The arrangement is such that when mucus sample 50 is relatively watery (low viscosity), bias element 18 rotates probe 10 downwardly so that shank 14 is adjacent red segment 48. On the other hand, when mucus sample 50 is relatively tacky (high viscosity), bias element 18 is incapable of rotating probe 10 so that shank 14 remains adjacent green segment 46.

One process of the invention involves inserting sterile probe 10 through the vaginal cavity into contact with the cervix in order to obtain a sample of cervical mucus on bearing element 16. Next, with sections 26 and 28 in the opened or inoperative position as shown in FIG. 2, bearing 16 is placed into cavity 34. Then, sections 26 and 28 are closed and the cervical mucus is extruded between bearing surfaces 38 and 40, probe 10 and bearing member 12 being constrained for relative movement. Probe 10 is rotated manually a predetermined number of times, usually from one to three times. Next, shank 14 is placed in its upper most position adjacent green segment 46 as shown in FIG. 1. Probe 10 is then released. Finally, the rest position of shank 14 relative to green segment 46 and red segment 48 is indicative of menstrual cycle phase, i.e. the presence or absence of ovulation.

An alternative process involves inserting sterile probe 10 into the mouth in order to obtain a sample of oral mucus, i.e. saliva, on bearing element 16. This process otherwise is identical to that heretofore described in connection with the cervical mucus sample.

Referring now to FIGS. 5-10, there is shown alternate embodiments of the invention in the form of an instrument 58 for obtaining and testing a cervical mucus sample in order to determine menstrual cycle phase. Instrument 58 is generally comprised of an outer sleeve or sheath 60, a removable coaxial core 62, a removable, coaxial, spring-loaded plunger 64 and a tester 66.

Outer sleeve 60 is in the form of an elongated tubular member which is perferably 6 to 12 inches in length and ½ to 1½ inches in diameter. Sleeve 60 is formed with an annular flange 68 at the outer end thereof which serves the dual purpose of functioning as a stop for sleeve 60 and as a stop for core 62. Preferably, sleeve 60 is composed of a dimensionally stable, sterilizable material, for example, a vitreous material such as glass, a mwetallic material such as glass, a metallic material such as stainless steel, or a plastic material such as methyl methacrylate.

Core 62 is of generally cylindrical configuration formed with an annular shoulder 70 which cooperates with flange 68 on sleeve 60 to limit the movement of core 62 into sleeve 60. Preferably core 62 is composed of a dimensionally stable, sterilizable material, for example, a vitreous material such as glass, a vitreous material such as glass, a metallic material such as stainless steel, or a plastic material such as methyl methacrylate. The forward end of core 62 is formed with a rounded tip 72 to facilitate insertion of the instrument. The dimensions of the outer diameter of core 62 and the inner diameter of sleeve 60 are such as to provide a snug, sliding fit therebetween. The function of core 62 is not only to facilitate insertion of the instrument, but also to prevent contamination of the exposed surface of plunger 64 with secretion present along the walls of the vaginal cavity. The overall length of core 62 exceeds that of sleeve 60 so that rounded tip 22 extends through the forward end of sleeve 60 while the opposite end extends out through the other end of sleeve 60 where it may be manually grasped for removal. To this end, shoulder 70 is of somewhat smaller diameter than the flange 68 so that core 62 may be removed separately from sleeve 60.

In practice, assembled sleeve 60 and core 62 are inserted through the vaginal cavity with rounded tip 22 positioned in close proximity to the cervix. With the instrument in position, core 62 is then withdrawn leaving the sleeve 60 in place. Thereupon, plunger 64 which is provided with a reduced tip portion 74 at its working end is inserted through sleeve 60. Tip 74 is pressed against the cervix and a sample specimen of cervical mucus is accumulated thereon. It will be noted that plunger 64 is generally about the same length as core 62 except that tip 74 is of a reduced diameter. The shank of plunger 64 corresponds in outside diameter with the inside diameter of sleeve 60. Reduced tip portion 74 is cylindrical having an approximate axial length of ½ to 1½ inches, for example. The opposite end of plunger 64 is formed with a flange 76 and, in the preferred mode of the invention, a coil spring 78 is trapped between plunger flange 76 and sleeve flange 68. Thus, plunger flange 76 can be pressed inwardly so that reduced tip 74 extends outwardly to bear against the cervix and pick up a cervical mucus specimen 77. When plunger 64 is released, tip 74 is automatically retracted into sleeve 60 as suggested in FIG. 7. In the retracted position, cervical mucus specimen 77 carried on tip 74 is protected by sleeve 60. Both sleeve 60 and plunger 64 now may be withdrawn from the vaginal cavity withiiut mucus specimen 77 being wiped away or contaiminated during removal. Plunger 64 may be fabricated from a variety of materials but the material should have a relatively low coefficient of thermal expansion for reasons that will presently appear. Various moldable plastics are available which have coefficients of expansion close to zero and may be used to advantage. Preferably, plunger 64 is composed of dimensionally stable, sterilizable material, for example, a vitreous material such as glass, a metallic material such as stainless steel, or a plastic material such as methyl methacrylate.

Once the instrument has been withdrawn, plunger 64 is separated from sleeve 60, taking care to avoid wiping of the collected mucus specimen from tip 74. Once separated, the viscosity of the specimen is measured by placing tester 66, for example a viscometer ring 66 over reduced tip 74 so that specimen mucus 77 is extruded between ring 66 and tip 74. Ring 66 is provided with an off-center weight 79 which, in the FIG. 8 embodiment, is mounted to a lever arm or stem 80 mounted chordally to ring 66 and extending to one side thereof. Stem 80 and weight 79 thus provide a moment arm for ring 66 as part of the viscosity measuring device. In the use of this device, absolute viscosity is not determined. Rather it is of interest only to measure changes during the menstrual cycle. Thus, the instrument might be more aptly described as a comparator device.

Stem 80 may be slidably connected to the ring or the weight 79 may be slidably mounted along the stem in order to change the moment arm with respect to ring 66. In either event, the effective length of the moment arm is employed as the determining factor with regard to the viscosity of the mucus sample. In the preferred form of the invention, assuming stem 80 is fixed to ring 66 and weight 79 is movable along the stem 80, stem 80 may be color coded using, for example, a red band 82 near ring 66 and a green band 84 at the outer end of stem 80. If the specimen is of low viscosity, the ring 66 will turn easily with respect to plunger tip 74, this being determined by placing the weight 79 close to ring 66 and somewhere over red band 82 of stem 80. Thus, if ring 66 turns easily under these conditions, it is an indication that ovulation recently occurred, is now occurring or is about to occur. If on the other hand, the specimen is highly viscous, ring 66 will not turn easily and weight 79 would have to be moved towards the end of the stem over green band 84. If ring 66 turns only with weight 79 over green band 84, this indicates that the specimen has high viscosity and therefore ovulation is not occurring.

In the preferred form of the invention, reduced tip 74 has an axial length in the range of 10 to 12 millimeters and the ring 66 has an axial length of 10 millimeters. The moment arm provided by stem 80 should be on the order of 10 centimeters and weight 78 should be on the order of 1 to 3 grams. Preferably, the radius of reduced tip 74 is approximately 5.0 millimeters while the inside radius of ring 66 is approximately 5.1 millimeters. In accordance with the present invention, an outer bearing surface 83 of tip 74 and an inner bearing surface 85 of ring 66 requires a grit size ranging from 200 to 800 grains per square inch and preferably from 400 to 600 grains per square inch. Also, the spacing or tolerance between bearing surfaces 83 and 85 ranges from 0.01 to 10.0 mils and preferably from 1 to 5 mils. Obviously when used with animals, the sizes should be proportional, larger or smaller to accomodate the size of the vaginal canal.

Figure 9:
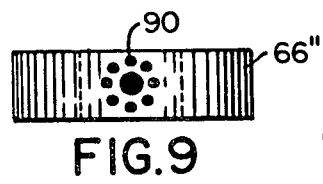
FIG. 9 is a perspective view showing a modified viscometer ring.

Referring now to FIG. 9 of the drawings, there is illustrated a further modification of the invention. In this embodiment a viscometer ring 66' is provided with a weight 86 on the end of a string 88 wrapped about and attached to the ring 66'. Ring 66' is used in a fashion similar to that of the FIG. 8 embodiment and is placed over reduced tip 74 carrying the cervical mucus specimen. If weight 78 is sufficient to produce enough torque on the ring to rotate it, this will be equivalent to about 50 to 100 poise indicating low viscosity of the mucus. If desired, the flat face of the ring 66' and the flat face of tip 74 may be provided with reference marks to be sure that the ring is mounted in the proper fashion and also provide an indication of movement.

Figure 10:
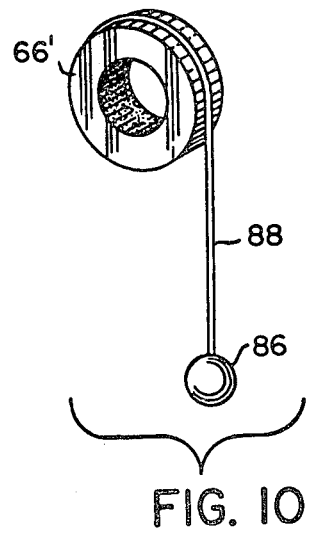
FIG. 10 is a side view of another modification of the viscometer ring.

Referring now to FIG. 10, there is illustrated a further modification of the invention. In this embodiment, a viscometer ring 66" is fabricated of a transparent material and provided with indicia 90 on one side of the cylindrical outer face thereof. Indicia 90 may be in any of a variety of patterns such as single large circle surrounded by a concentric ring of smaller circles as shown in FIG. 10. Alternatively, a set of parallel lines or a pattern of circles in a cross arrangement may be employed. In any event, ring 66" is employed to determine the optical clarity of the mucus specimen and may be used by itself or preferably in conjunction with either of the embodiments shown in FIGS. 8 and 9 as a means for verifying the conclusions as to the condition of the mucus. As previously indicated, the mucus will be relatively clear near the time of ovulation and relatively opaque at other times. This condition of the mucus may be determined by placing ring 66" over tip 74 carrying the specimen thereon. Next, ring 66" is turned to spread the mucus specimen evenly over tip 74 and within ring 66". Having done this, ring 66" is removed and held so that indicia 90 are facing away from the viewer. If indicia pattern 90 appears clearly defined, this indicates that the specimen has high optical clarity indicative of cervical mucus taken at or near the time of ovulation. If on the other hand, indicia pattern 90 is blurred so as to appear as a single large circle, this indicates that the mucus is opaque and the time of ovulation is not near.

It will be understood that, in alternate embodiments of FIGS. 5–10, instead of the rotary type arrangement for evaluating the viscosity of the mucus sample, plunger 64 may be formed with an elongaged reduced tip portion so that with the sample on the tip and the plunger held upright, the ring may be placed over the tip. In this arrangement, if the ring slides down the tip it is an indication of low viscosity. Weights may be added to the ring is desired and the reduced tip may be color-coded, for example the upper part having a green band, and the lower part having a red band.

The instrument may be employed on humans or animals with appropriate changes in dimensions of the instrument.

Since certain changes may be made in the foregoing disclosure without departing from the scope of the invention herein involved, it is intended that all matter contained in the above description and depicted in the accompanying drawings be construed in an illustrative and not in a limiting sense.

What is claimed is:

1. Apparatus for menstrual cycle phase determination, said apparatus comprising:
   (a) rod means including forward tip means and rearward handle means;
   (b) ring means for receiving said forward tip means and bias means for causing rotation of said ring means with respect to said tip means;
   (c) said rod means being operative for insertion into the vaginal cavity in order to cause said forward tip means to contact the uterus and to retrieve a mucus specimen;
   (d) said forward tip means being characterized by a first cylindrical bearing surface;
   (e) said ring means being characterized by a second cylindrical bearing surface;
   (f) said forward tip means and said ring means being operative to mate with said mucus specimen between said first cylindrical bearing surface and said second cylindrical bearing surface;
   (g) said bias means being operative to exert force between said forward tip means and said ring means when said first cylindrical bearing surface and said second cylindrical bearing surface are mated;
   (h) and indicia means for indicating the degree of such force as a function of the physical character of said specimen;
   (i) said forward tip means and said ring means being readily separable and readily matable;
   (j) said bias means being an adjustable eccentric weight.

* * * * *